US011273051B2

(12) United States Patent
Neary

(10) Patent No.: US 11,273,051 B2
(45) Date of Patent: Mar. 15, 2022

(54) OSTEOCONDUCTIVE DEVICES AND METHODS OF USE

(71) Applicant: Douglas Neary, Santa Ana, CA (US)

(72) Inventor: Douglas Neary, Santa Ana, CA (US)

(*) Notice: Subject to any disclaimer, the term of this patent is extended or adjusted under 35 U.S.C. 154(b) by 0 days.

(21) Appl. No.: 16/532,982

(22) Filed: Aug. 6, 2019

(65) Prior Publication Data

US 2021/0038403 A1 Feb. 11, 2021

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2002/3093* (2013.01); *A61F 2002/30263* (2013.01); *A61F 2002/30593* (2013.01); *A61F 2002/30785* (2013.01); *A61F 2002/30828* (2013.01)

(58) Field of Classification Search
CPC .. A61F 2/447; A61F 2/446; A61F 2/04; A61F 2/65; A61F 2/4455; A61F 2/44; A61F 2/4465
See application file for complete search history.

(56) References Cited

U.S. PATENT DOCUMENTS

| 2012/0191188 A1* | 7/2012 | Huang ..................... A61F 2/447 |
| | | 623/17.11 |
| 2014/0277491 A1* | 9/2014 | Fang ....................... A61F 2/447 |
| | | 623/17.16 |
| 2020/0188130 A1* | 6/2020 | Jebsen .................... A61F 2/447 |

FOREIGN PATENT DOCUMENTS

FR          2977474 A1 *  1/2013  ............ A61F 2/4611

OTHER PUBLICATIONS

English translation of FR 2977474. (Year: 2013).*

* cited by examiner

*Primary Examiner* — Amy R Sipp
(74) *Attorney, Agent, or Firm* — John M. Behles

(57) ABSTRACT

Osteoconductive devices and methods of use are provided herein. An example device includes a hollow body member having surfaces, the hollow body member having a shape that substantially conforms to a cross-sectional area of an opening of an orthopedic prosthesis, and apertures formed in the surfaces of the hollow body member that provide a osteoconductive path through the hollow body member.

12 Claims, 8 Drawing Sheets

OSTEOCONDUCTIVE DEVICES AND METHODS OF USE

CROSS-REFERENCE(S) TO RELATED APPLICATIONS

N/A

TECHNICAL FIELD

The present disclosure relates to orthopedic implants devices and methods, and more specifically, but not by way of limitation, to osteoconductive devices and methods that are configured to enhance bone growth through an orthopedic prosthesis.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Figure 1:
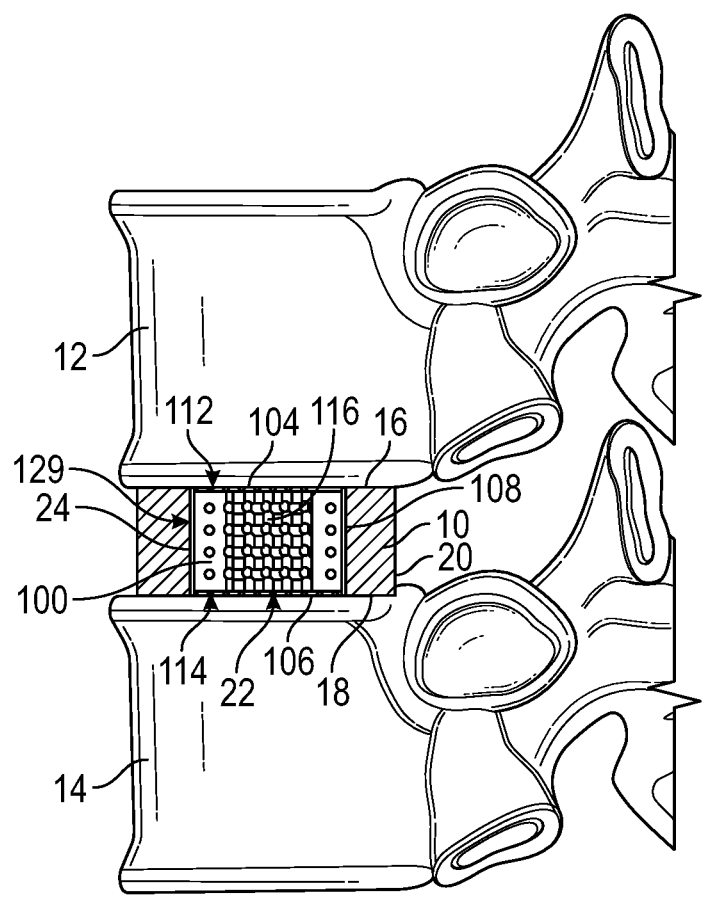
FIG. 1 is a cross-sectional view of an environment where an example system of the present disclosure is deployed in an example use case.

Generally, the present disclosure relates to osteoconductive devices and methods of their use. In one embodiment, an example osteoconductive device of the present disclosure includes a body member that is configured to be inserted into an orthopedic prosthesis. The body member can be any of hollow and/or porous.

In one example, the orthopedic prosthesis could include an interbody fusion cage having an opening (also referred to as a graft space). An example osteoconductive device of the present disclosure can be inserted into the opening of the interbody fusion cage to at least partially fill the opening. In various embodiments, the presence of the osteoconductive device enhances bone growth through and/or around the interbody fusion cage.

For context, orthopedic prostheses, such as interbody fusion cages, are often manufactured from polymeric or thermoplastic materials such as polyether-ether-ketone (PEEK). PEEK is often utilized due to the fact that it possesses an elastic modulus similar to bone. PEEK is also radiolucent and has favorable biocompatibility characteristics. For example, a characteristic of PEEK's biocompatibility is that it is osteotolerant. Its surface characteristics do not generally hinder nor propagate bone fusion near the material. In some instances, PEEK orthopedic prostheses can be encapsulated with a thin fibrous tissue layer to improve osteoconductivity that is above and beyond that of the PEEK material alone. Thus, while being ostetolerant, PEEK is not osteoconductive or osteoenhancing.

In contrast, the osteoconductive devices of the present disclosure can be utilized in combination with an orthopedic prosthesis to enhance fusion of the orthopedic prosthesis with surrounding bone surfaces. In various embodiments, an example osteoconductive device of the present disclosure can be inserted into an opening of an orthopedic prosthesis. Over time, bone can migrate through the osteoconductive device to enhance fusion of the orthopedic prosthesis with surrounding bone surfaces. In one example embodiment, an osteoconductive device includes a generally cuboid, hollow and porous body member that is shaped to conform to a centrally located pass-through opening (e.g., graft opening) of an interbody fusion cage. Generally, the interbody fusion cage is installed between two vertically adjacent vertebral bodies, and within an in intervertebral disc space.

The osteoconductive device can be press-fit into the opening of the orthopedic prosthesis in some embodiments. The porosity of the osteoconductive device creates osteoconductive paths through which bone from either or both of the two vertically adjacent vertebral bodies may migrate over time and fuse with the osteoconductive device. The osteoconductive device allows for fusion of the interbody fusion cage with the two vertically adjacent vertebral bodies in a way that would be impossible with the interbody fusion cage alone. In various embodiments, osteoconductive devices disclosed herein can include an internally fixed osteoconductive titanium insert. Device designs and methods are disclosed for forming and manufacturing a titanium-based porous insert (e.g., osteoconductive device). To be sure, other materials can also be used to create the osteoconductive device. These and other advantages of the present disclosure are provided in greater detail herein with reference to the collective drawings.

Illustrative Embodiments

Figure 2A:
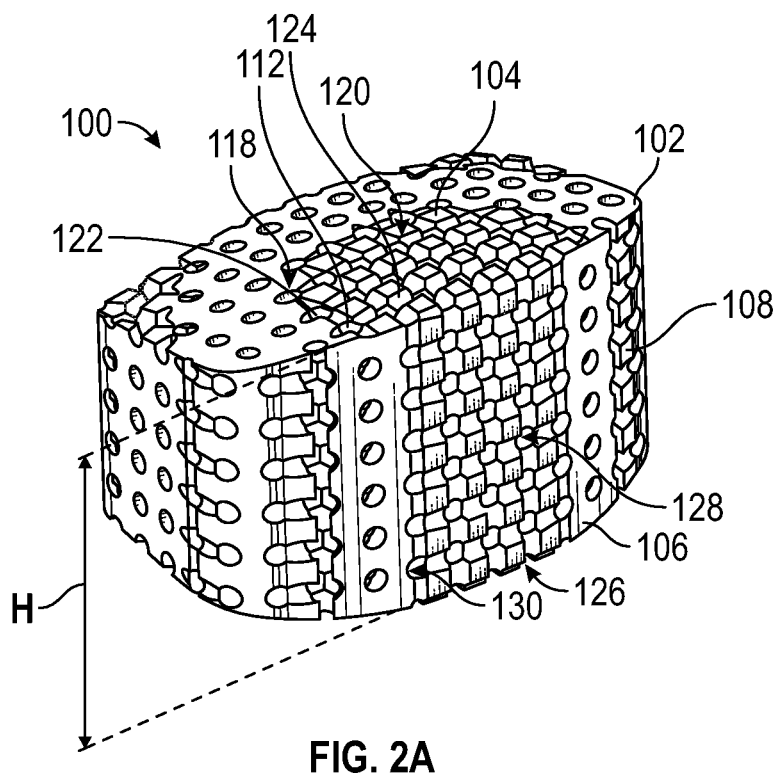
FIGS. 2A-2C collectively illustrate an example embodiment of an osteoconductive device for use in combination with an orthopedic prosthesis.
Figure 2B:
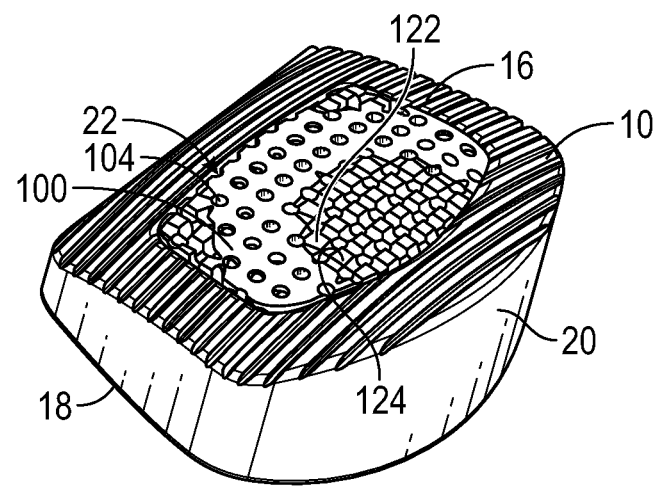
Figure 2C:
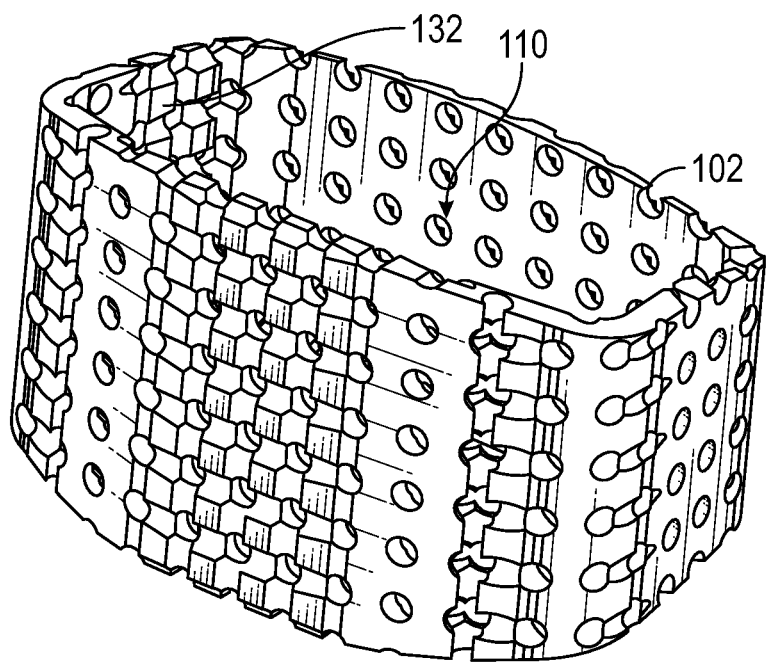

Turning now to the drawings, FIGS. 1-2C collectively depict an illustrative environment in which techniques and structures of the present disclosure may be implemented. Generally, an example orthopedic prosthesis 10, such as an interbody fusion cage is illustrated as being placed between two vertically adjacent vertebral bodies 12 and 14. While an interbody fusion cage is disclosed as an example, the present disclosure can be adapted for use in other similarly constructed orthopedic prostheses. Thus, the disclosure should not be limited to only the example orthopedic prostheses disclosed herein.

For context, the orthopedic prosthesis 10 is used to replace an intervertebral disc (not shown) between the two vertically adjacent vertebral bodies 12 and 14. In some embodiments, the intervertebral disc can be removed due to damage. An example procedure that may be used to remove a damaged vertebral body includes a discectomy. Generally, the orthopedic prosthesis 10 is placed into a space where the intervertebral disc once existed. The orthopedic prosthesis 10 can be affixed to each of the two vertically adjacent vertebral bodies 12 and 14 using pedicle screws (not shown). Other methods for coupling the orthopedic prosthesis 10 can also be utilized, as would be known to one of ordinary skill in the art.

The mechanical coupling of the orthopedic prosthesis 10 with the two vertically adjacent vertebral bodies 12 and 14 creates a mechanical fusion. In some embodiments, the shape of various surfaces of the orthopedic prosthesis 10 may substantially correspond to a shape of an intervertebral disc.

As noted above, the orthopedic prosthesis 10 has a generally cuboid shape having a first surface 16 (e.g., upper surface or endplate), a second surface 18 (e.g., lower surface or endplate), a sidewall 20, and an opening 22. The opening 22 defines a bone fusion channel of the orthopedic prosthesis 10. In some embodiments, the orthopedic prosthesis 10 is manufactured from PEEK, but other materials that are biocompatible can also be utilized.

The opening 22 is defined by an inner surface or sidewall 24. A size and shape of the opening 22 can vary according to design requirements. In various embodiments, the opening 22 extends between the first surface 16 and the second surface 18.

According to some embodiments, an osteoconductive device 100 can be inserted into the opening 22 of the orthopedic prosthesis 10. A perspective view of the osteoconductive device 100 is illustrated in FIG. 2A. A perspective view of the osteoconductive device 100 in combination with the orthopedic prosthesis 10 is illustrated in FIG. 2B. In various embodiments, the osteoconductive device 100 is an insert that comprises a body member 102 having a plurality of surfaces, such as a first surface 104 and a second surface 106, as well as a sidewall 108. In some embodiments the body member 102 is substantially hollow. That is, each of the surfaces and the sidewall of the body member 102 has a given thickness, which results in the creation of a cavity 110 as best illustrated in FIG. 2C, which illustrates the body member 102 with the first and second surfaces removed. In other embodiments, the body member 102 can be solid rather than substantially hollow.

In one or more embodiments, the sidewall 108 can be formed from one or more polygonal surfaces/facets that are connected together into a continuous member. In other embodiments, the sidewall 108 can include a continuous smooth surface. In general, the sidewall 108 spaces apart the first surface 104 and the second surface 106. In general, the osteoconductive device 100 has a shape that conforms substantially to an inner cross-sectional area of the opening 22 of the orthopedic prosthesis 10. In some embodiments, the outer geometry of the sidewall 108 is configured to correspond to the inner surface or sidewall 24 of the opening 22 of the orthopedic prosthesis 10. This shape correspondence allows the sidewall 108 of the osteoconductive device 100 to contact the inner surface or sidewall 24 of the opening 22 of the orthopedic prosthesis 10 when the osteoconductive device 100 is inserted into the opening 22 of the orthopedic prosthesis 10.

The osteoconductive device 100 has a height dimension H that is measured from the first surface 104 to the second surface 106. In various instances, the height dimension H is selected such that the first surface 104 of the body member 102 is aligned with (e.g., coplanar or flush) with the first surface 16 of the orthopedic prosthesis 10. Likewise, the second surface 106 of the substantially hollow body member 102 is aligned with (e.g., coplanar or flush) with the second surface 18 of the orthopedic prosthesis 10.

In various embodiments, the body member 102 may at least partially or completely fill the opening 22 of the orthopedic prosthesis 10. The alignment of the surfaces of the body member 102 with the orthopedic prosthesis 10 allows for the first surface 104 of the body member 102 and the second surface 106 of the body member 102 to contact surface of the two vertically adjacent vertebral bodies 12 and 14. For example, the first surface 104 of the body member 102 contacts the vertebral body 12 and the second surface 106 of the body member 102 contacts the vertebral body 14. This mating contact allows for osteoconductive behavior between the vertebral bodies and the osteoconductive device 100.

To further improve the osteoconductive properties of the osteoconductive device 100, the body member 102 comprises a plurality of apertures, such as an aperture 112 associated with the first surface 104 and an aperture 114 (see FIG. 1) associated with the second surface 106. Thus, the body member 102 can be porous in some embodiments. The degree of porosity of the body member 102 depends proportionally to the number of apertures. In various embodiments each of the surfaces of the body member 102, such as the first surface 104, the second surface 106, and the sidewall 108 are provided with apertures. In other embodiments, only the first surface 104 and the second surface 106 may include apertures. Apertures, regardless of the surface onto which they are manufactured, provide an osteoconductive path into the cavity 110 of the osteoconductive device 100.

When both the first surface 104 and the second surface 106 each include apertures, one or more osteoconductive paths can be created through the body member 102. For example, bone material 116 can migrate from the vertebral body 12, through the aperture 112 associated with the first surface 104, and into the cavity 110. In some instance, the bone material 116 may cross the cavity 110 and pass through the aperture 114 associated with the second surface 106. Regardless of whether the bone material 116 enters into the cavity 110 only, or migrates across from one vertebral body 12 to the other vertebral body 14, a fusion process occurs which links the vertebral body 12, the osteoconductive device 100 and orthopedic prosthesis 10, and the vertebral body 14 together. Stated otherwise, the apertures provide cannulation that allows bone material to enter into the body member 102, and in some embodiments, create bone fusion with the vertebral bodies. In some embodiment, the bone material 116 can invade and occupy all or a substantial portion of the cavity 110 of the body member 102.

In various embodiments, the apertures are aligned in rows, such as row 118. In other embodiments, the apertures can be placed randomly or irregularly across a surface. The apertures can have any desired shape. In some embodiments, the shapes of the aperture can vary within a row, or the shapes can vary from row-to-row or from surface-to-surface.

According to some embodiments, either or both of the first surface 104 and the second surface 106 can comprise additional porosity or surface roughening to favorably increase an available surface chemistry of the surfaces (e.g., increase surface area for bonding with bone material), reduce stiffness of the osteoconductive device 100 overall, and increase radiolucency of the osteoconductive device 100. For example, section 120 of the first surface 104 of the body member 102 includes surface trenching. For example, a trench 122 can be created across at least a portion of the row 118 of apertures. When trenching occurs across rows of apertures in two or more directions, surface objects or artifacts are created, such as surface object 124. The shape and size of these surface objects depends on the shape and number of trenches on the surface. The surface objects provide anchoring points for engaging with the bony surface of a vertebral body, which enhances surface chemistry and fusion between the osteoconductive device 100 and the vertebral body. Trenching in two or more directions can also create an interconnected grid or matrix, which can be filled with bone material.

In some embodiments, the surfaces of the body member 102 can be enhanced with porosity through texturing. For example, a mechanical abrading process can be used to create surface texture. In another embodiment, processes such as sputtering or vapor/chemical deposition can be used to create nano-structures on one or more of the surfaces of the body member 102. In other embodiments, additive manufacturing can be used. To be sure, additive manufacturing can also be used to create the osteoconductive device 100 itself.

In various embodiments, trenching can occur across apertures of the sidewall 108 as well. For example, trench 126 can be created along a row of apertures 128 formed in the sidewall 108. The trench 126 provides another osteoconductive path for growth of bone material. As best illustrated in FIG. 1, when the osteoconductive device 100 is coupled with the orthopedic prosthesis 10, the inner surface or sidewall 24 of the opening 22 of the orthopedic prosthesis 10 cooperates with the sidewall 108 to create an enclosed osteoconductive path 129. The enclosed osteoconductive path 129 is a tubular tunnel that allows bone material to be conducted from both the vertebral bodies 12 and 14. Thus, the bone material can conduct both through the cavity 110 of the osteoconductive device 100 as disclosed above, as well as around the enclosed osteoconductive path 129. When trenching occurs in multiple directions across the sidewall 108, objects can be created (such as surface object 124 disclosed above), as well as series of interconnected trenches (e.g. vertical and horizontal trenches). Referring back to FIG. 2A, while the trench 126 is vertically oriented, another trench 130 can be horizontally oriented. When multiple vertical and horizontal trenches are present, an interconnected grid or matrix is created, which can be filled with bone material when the osteoconductive device 100 contacts bone. In some embodiments, trenching can be used across the entirety of a surface, or only a portion thereof.

Figure 3:
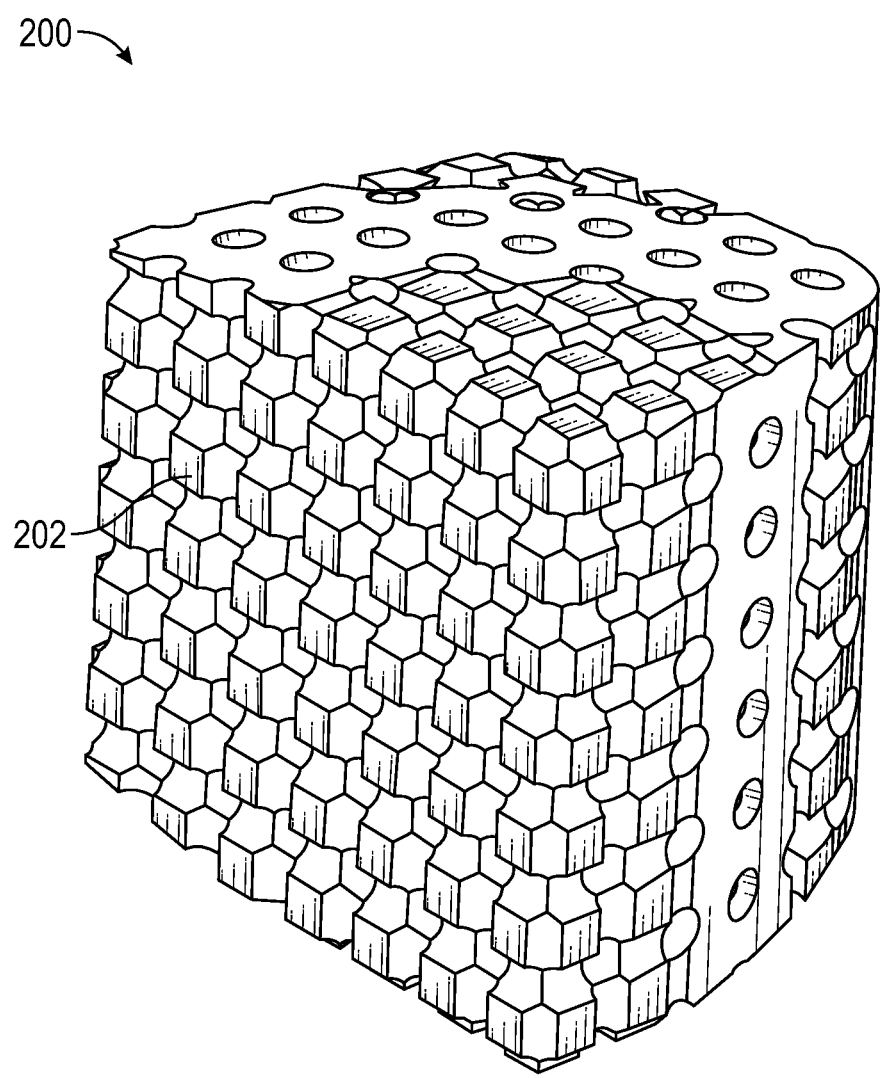
FIG. 3 is a perspective view of another example embodiment of an osteoconductive device.

When the osteoconductive device 100 is inserted into the orthopedic prosthesis 10 and the combination is installed between vertebral bodies, bone material can conduct through the matrices of the surfaces and into the cavity 110 of the body member 102, as well as across the sidewall 108 (if a matrix is present on the sidewall 108). Thus, some bone material may conduct across the sidewall 108. When apertures are present on the sidewall 108, a trench matrix created on the sidewall 108 may allow bone material to enter through the apertures of the sidewall 108 (for example the row of apertures 128 formed in the sidewall 108). In some embodiments, the sidewall 108 may be trenched but not include apertures. In these embodiments, bone material can extend across the face of the sidewall 108 through the trenches. An example osteoconductive device 200 having at least one trenched surface 202 without apertures is illustrated in FIG. 3, which is disclosed in greater detail infra.

Referring back to FIG. 2C, it will be understood that an inner surface 132 of the body member 102 can be trenched to create a trench matrix that includes surface objects. The bone material can integrate into this trench matrix as well as extending through any apertures that may be present in the surface/sidewall.

According to some embodiments, the osteoconductive device 100 can comprise an osteogrowth enhancing material disposed within the cavity 110 of the body member 102. For example, an osteogrowth enhancing material could include autologous tissue or bone material. In another example, the osteoconductive device 100 can comprise a medicament or a combination of an osteogrowth enhancing material and a medicament. In another embodiment, the apertures of the osteoconductive device 100 can be packed with an osteogrowth enhancing material and/or a medicament. Example medicaments could include any medicament that is configured to reduce infection, improve wound healing, and/or promote bone growth.

In use, the osteoconductive device 100 can be coupled with the orthopedic prosthesis 10 using a compression fit. That is, the osteoconductive device 100 can be press-fit into the opening 22 of the orthopedic prosthesis 10 such that the sidewall 108 of the osteoconductive device 100 contacts (at least partially) the inner surface or sidewall 24 of the opening 22 of the orthopedic prosthesis 10. This insertion of the osteoconductive device 100 can occur pre-operatively or intraoperatively by a user. Also, the first surface 104 of the osteoconductive device 100 is aligned with the first surface 16 of the orthopedic prosthesis 10, while the second surface 106 of the osteoconductive device 100 is aligned with the second surface 18 of the orthopedic prosthesis 10. In other embodiments, rather than using a press or compression fit, the osteoconductive device 100 can be inserted into the orthopedic prosthesis 10 using a thermal fit.

In operation, a user of can obtain an osteoconductive device of the present disclosure and insert the osteoconductive device into an opening of a desired orthopedic prosthesis. In embodiments where an osteoconductive device is desired both internally and externally to the orthopedic prosthesis another osteoconductive device can be installed around an outer peripheral sidewall of the orthopedic prosthesis.

Once the osteoconductive device(s) and the orthopedic prosthesis are combined together, the combined system can be inserted or otherwise installed into an intervertebral disc space between two vertebral bodies. Again, one or more surfaces of the osteoconductive device(s) can sit flush with the endplates of the orthopedic prosthesis such that when the combined system is installed the one or more surfaces of the osteoconductive device(s) contact or are in near proximity to the vertebral bodies.

Figure 4A:
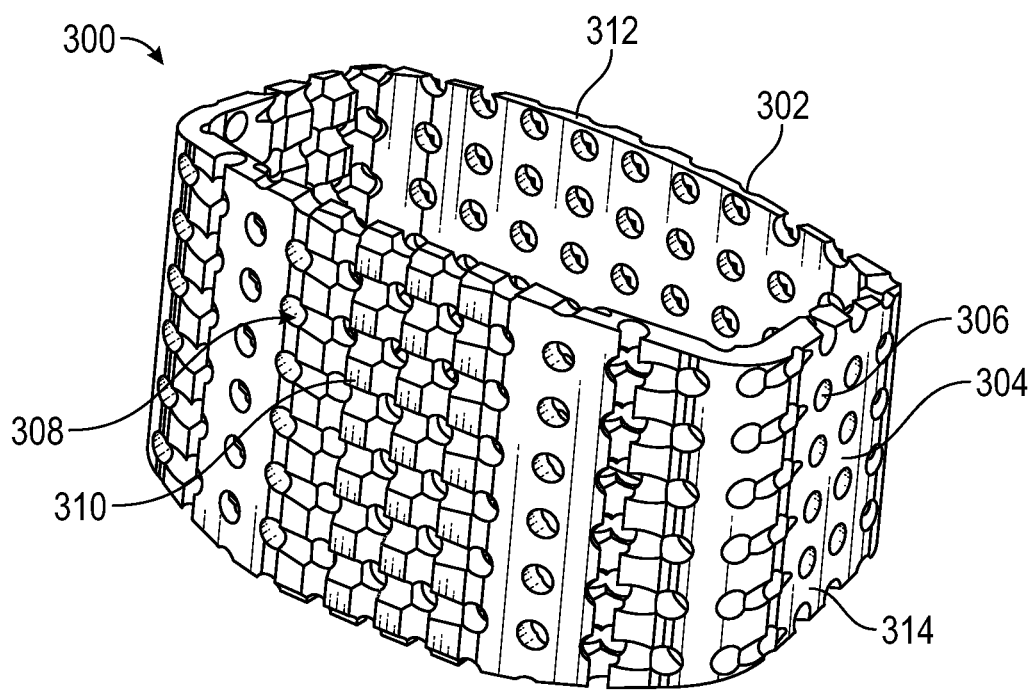
FIGS. 4A-4B collectively illustrate yet another example embodiment of an osteoconductive device for use in combination with an orthopedic prosthesis.
Figure 4B:
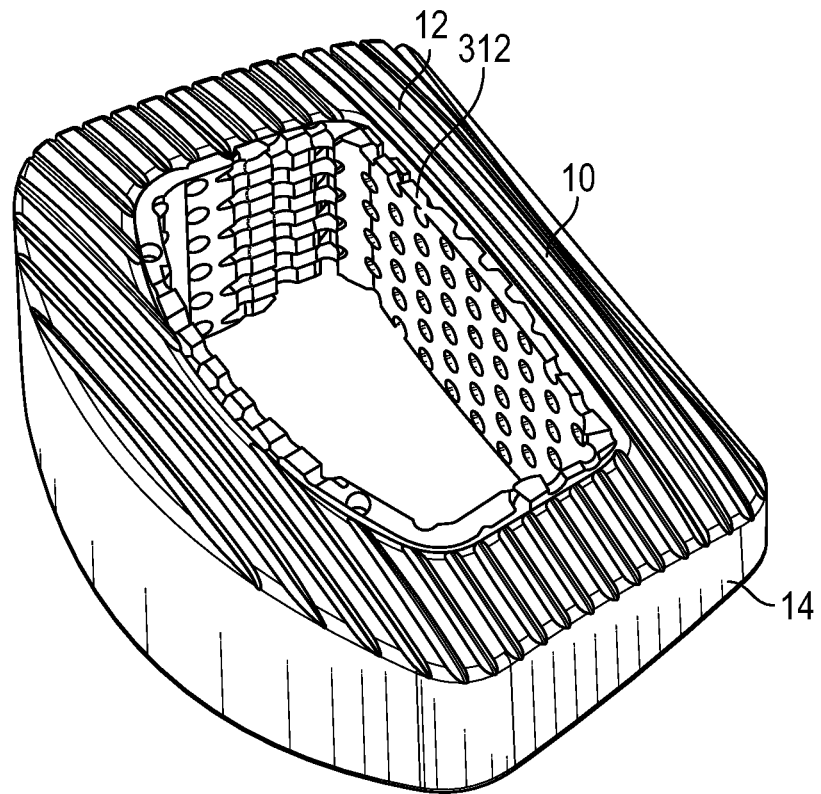

FIGS. 4A and 4B collectively illustrate another example osteoconductive device 300 that can be used with the orthopedic prosthesis 10. Generally, the osteoconductive device 300 comprises a body member 302 that comprises only a sidewall 304. The sidewall 304 is provided with a plurality of apertures, such as aperture 306. Trenching can be used across the plurality of apertures to create a textured surface or matrix 308 with surface objects, such as surface object 310. As with the embodiments, above, the matrix 308 comprises interconnected channels and a plurality of surface objects. When the osteoconductive device 300 is inserted into the orthopedic prosthesis 10, bone material can conduct through matrix both vertically and horizontally. For example, the bone material can conduct along the outer surface of the sidewall 304 within the trenches of the matrix 308. Bone material can also migrate or conduct into the apertures, such as aperture 306. To be sure, bone growth both vertically and horizontally provides a greater degree of fusion than bone growth in only a vertical direction or a horizontal direction. It will be understood that a thickness T of the sidewall 304 can vary according to design requirements. A height of the sidewall 304 can vary according to design requirements, but in some embodiments, a first edge 312 and a second edge 314 of the sidewall 304 can be aligned with the first surface 16 and the second surface 18 of the orthopedic prosthesis 10, respectively.

Figure 5A:
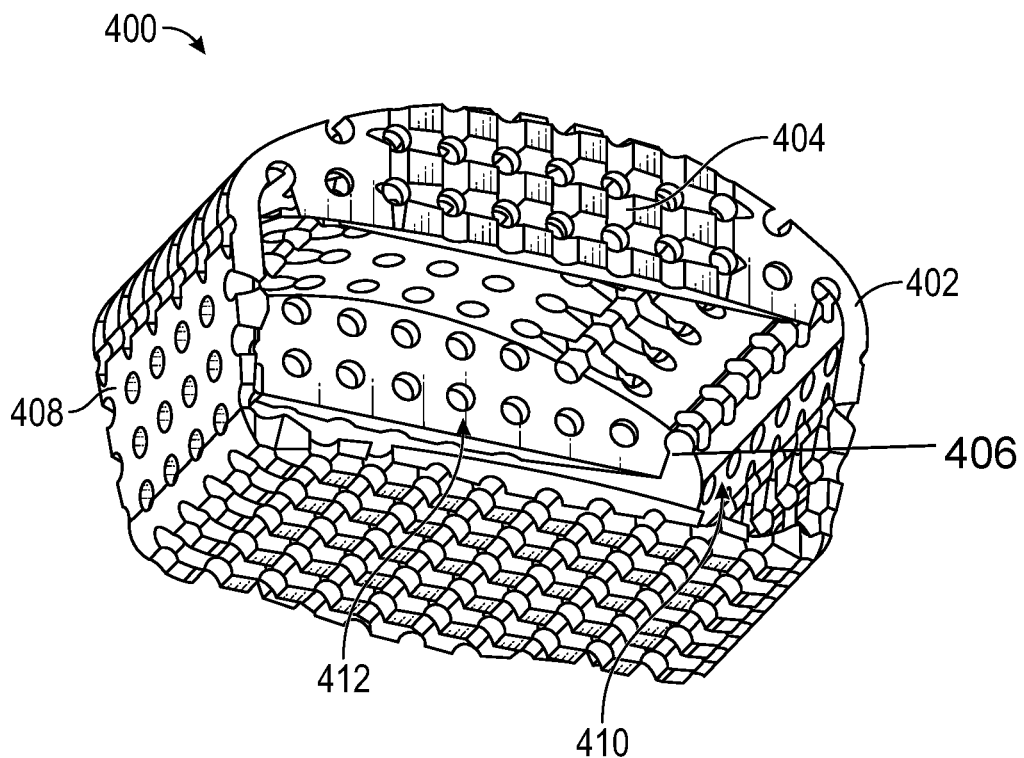
FIGS. 5A-5B collectively illustrate an additional example embodiment of an osteoconductive device for use in combination with an orthopedic prosthesis.
Figure 5B:
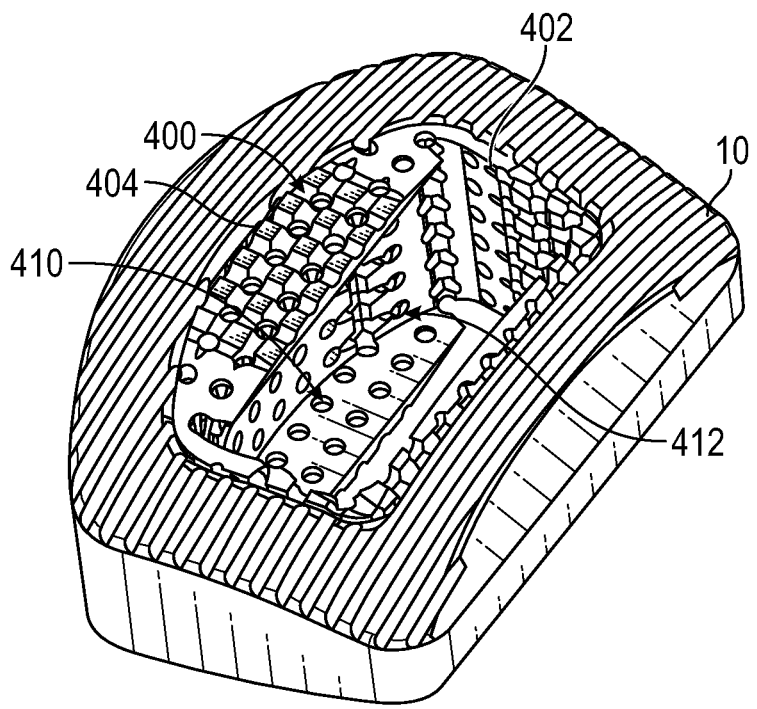

FIGS. 5A and 5B collectively illustrate another example osteoconductive device 400 that can be used with the orthopedic prosthesis 10. The osteoconductive device 400 comprises body member 402 having a first surface 404, a second surface 406, and a sidewall 408. In general, the first surface 404 terminates to create an upper shelf. The second surface 406 terminates to create a lower shelf. Thus, in comparison with the embodiment of FIGS. 2A-2B, the first surface 404 and the second surface 406 may not extend across and cover the sidewall 408 but terminate to create an opening 410. A gap or space 412 is created between the first surface 404 and the second surface 406.

Figure 6A:
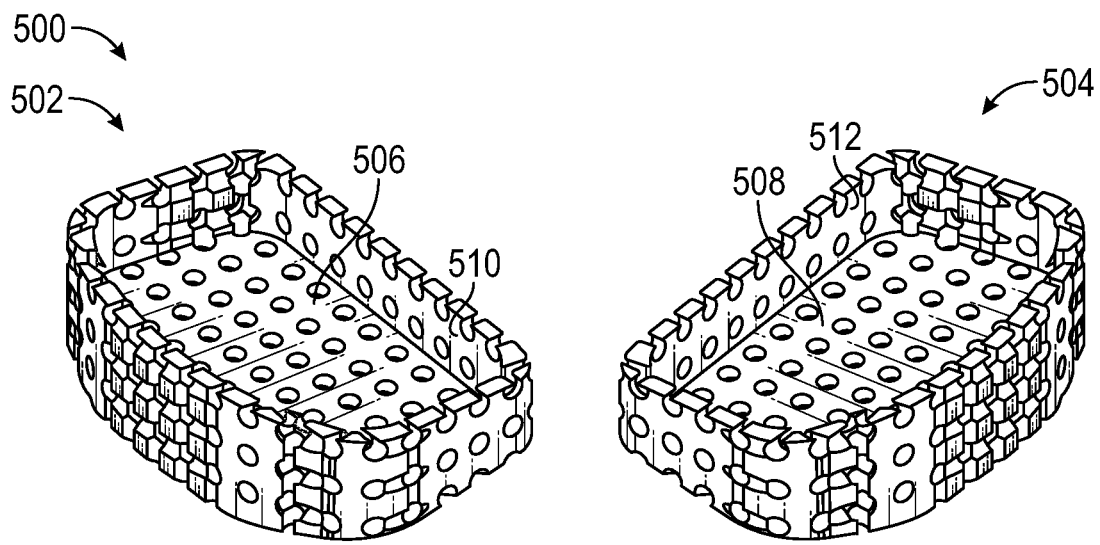
FIGS. 6A-6C collectively illustrate another example embodiment of an osteoconductive device for use in combination with an orthopedic prosthesis.
Figure 6B:
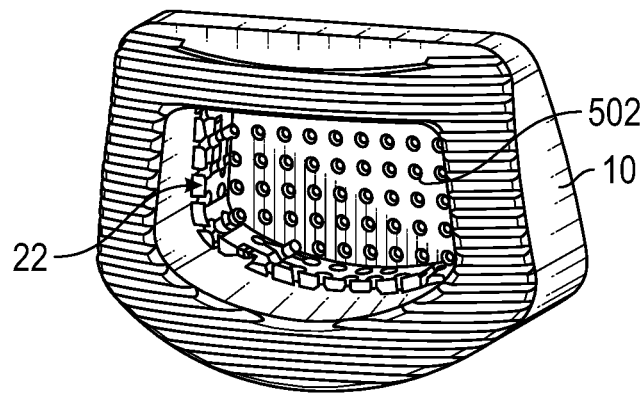
Figure 6C:
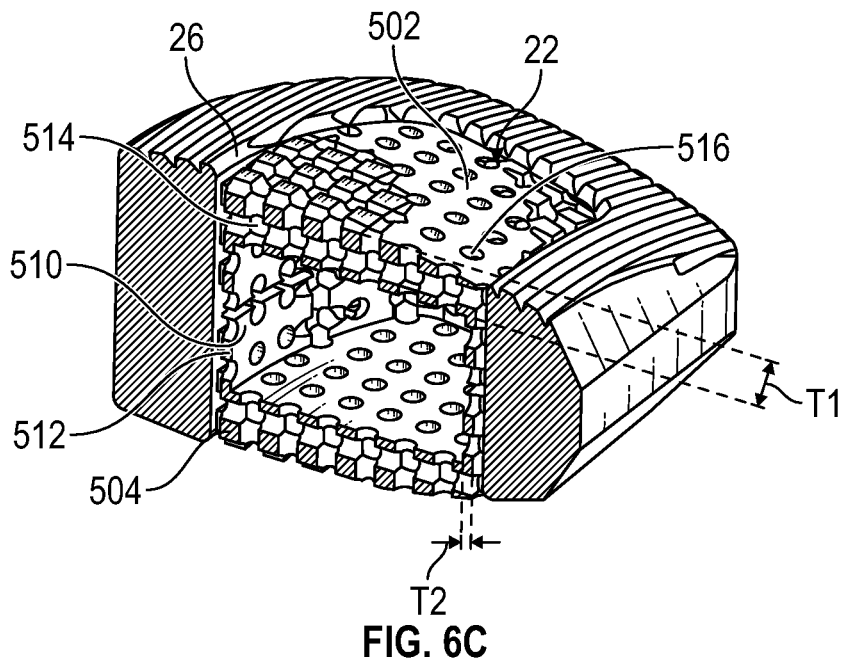

FIGS. 6A-6C collectively illustrate another example osteoconductive device 500 that can be used with the orthopedic prosthesis 10. In general, the osteoconductive device 500 comprises two portions 502 and 504. In some embodiments, the two portions 502 and 504 are identically constructed. Generally, the osteoconductive device 500 is similar or identical to the osteoconductive device 100 of FIGS. 2A-2B but the osteoconductive device is separated into two portions. In some embodiments, the osteoconductive device 500 comprises a first surface 506 and a second surface 508. The first portion 502 of the osteoconductive device 500 comprises the first surface 506 and a first sidewall 510 that extends normally to the first surface 506. The second portion 504 of the osteoconductive device 500 comprises the second surface 508 and a second sidewall 512 that extends normally to the second surface 508. In operation, the two portions 502 and 504 can be inserted into an opening 22 of the orthopedic prosthesis 10 in such a way that the first sidewall 510 mates with or is in close proximity to the second sidewall 512.

In various embodiments, the first surface 506 and the second surface 508 have transverse apertures. For example, the first surface 506 includes rows of transverse apertures, such as transverse aperture 514 that extend through a thickness dimension T1 of the first surface 506. In various embodiments, these rows of transverse apertures intersect with rows of apertures such as aperture 516. Thus, the rows of apertures extend in two directions, which in some instances include rows of apertures that are perpendicular to one another. In contrast, the first sidewall 510 includes apertures, such as aperture 516 that are oriented in only one direction. Also, it can be seen that a thickness dimension of the first sidewall 510 is less than the thickness dimension T2 of the first surface 506.

According to some embodiments, an edge 26 of the opening 22 of the orthopedic prosthesis 10 can be beveled, chamfered, or otherwise modified to create a transition from the osteoconductive device 500 to the endplates of the orthopedic prosthesis 10.

Figure 7A:
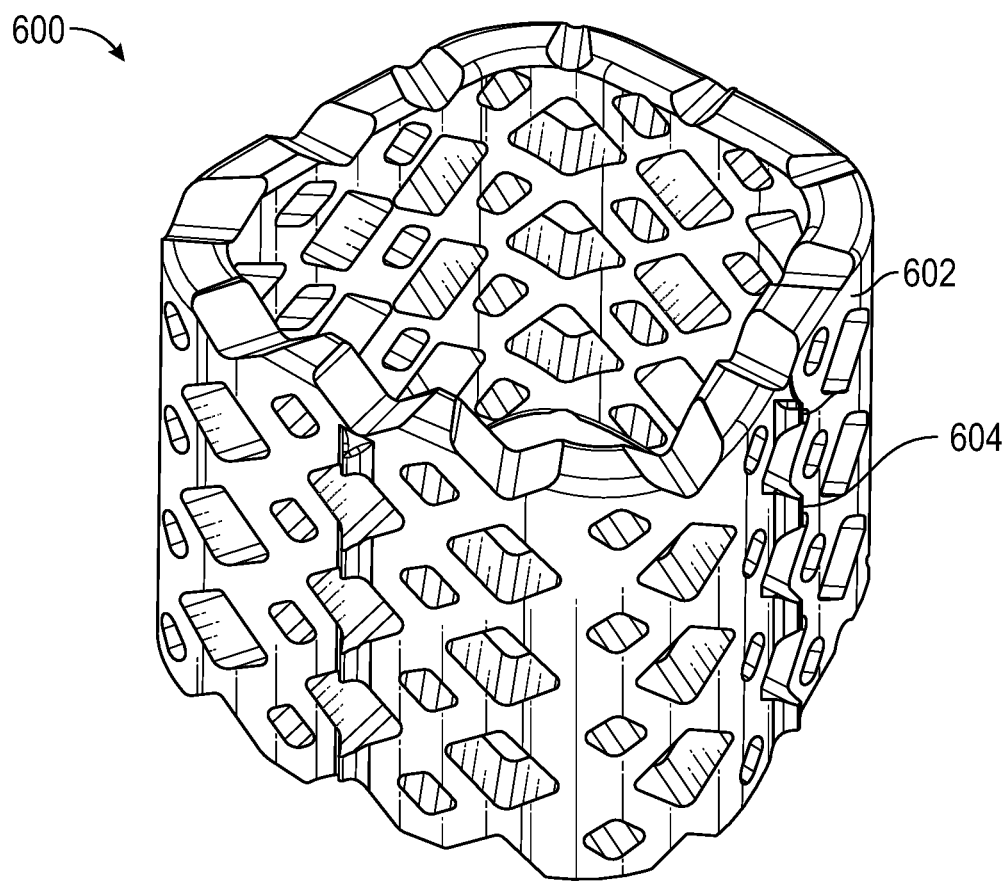
FIGS. 7A-7B collectively illustrate yet another example embodiment of an osteoconductive device for use in combination with an orthopedic prosthesis.

Some embodiments of osteoconductive devices can include securement or locking members that engage with an orthopedic prosthesis. For example, FIGS. 7A and 7B collectively illustrate an example osteoconductive device 600 that can couple with an orthopedic prosthesis 10 using securement members such as surface protrusions.

Figures 7B, 8:
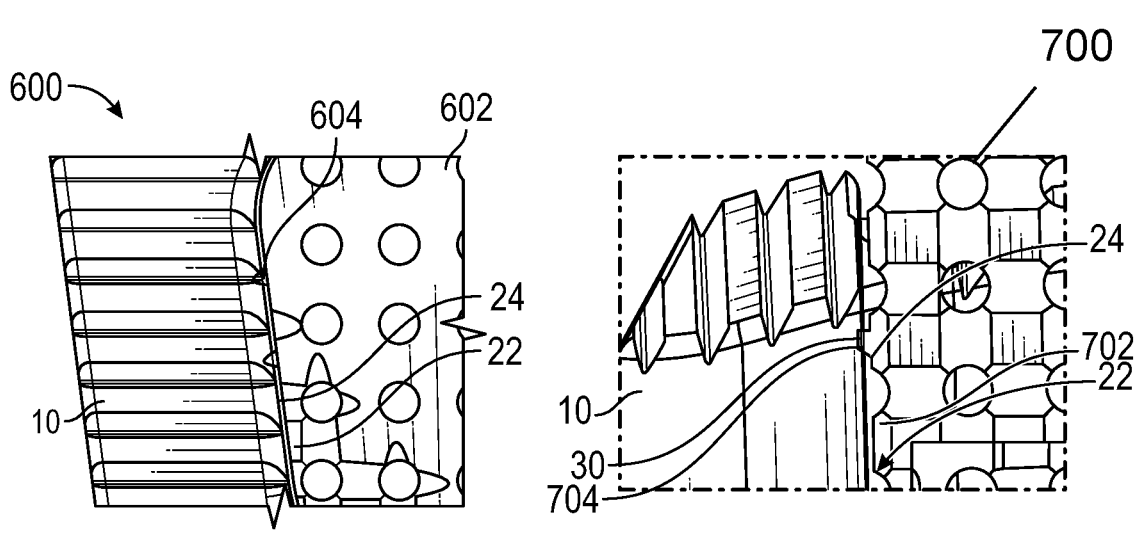
FIG. 8 is a close-up view of a portion of another example embodiment of an osteoconductive device.

The osteoconductive device 600 is similar in construction and structure to the osteoconductive device 300 of FIGS. 4A and 4B in that the osteoconductive device 600 includes only a sidewall 602. The sidewall 602 may comprise a plurality of protrusions, such as protrusion 604. The plurality of protrusions can include knurling or other similar surface feature that extends away from the sidewall 602. In FIG. 7B, the osteoconductive device 600 is illustrated inserted within an opening 22 of an orthopedic prosthesis 10. When inserted, the plurality of protrusions which bite into or otherwise engage with the inner surface or sidewall 24 of the opening 22 of the orthopedic prosthesis 10. When the plurality of protrusions embed into the inner surface or sidewall 24, the plurality of protrusions resist any tendency of the osteoconductive device 600 to disengage from the orthopedic prosthesis 10. To be sure, the protrusions disclosed with respect to the osteoconductive device 600 can be integrated into any of the osteoconductive devices disclosed herein.

FIG. 8 illustrates another securement means that couples an example osteoconductive device 700 with an orthopedic prosthesis 10. A sidewall 702 of the osteoconductive device 700 comprises an interference lip 704. When the osteoconductive device 700 is inserted into an opening 22 of an orthopedic prosthesis 10, the interference lip 704 flexes and locks into a groove 30 fabricated into an inner surface or sidewall 24 of the opening 22 of the orthopedic prosthesis 10. In some embodiments, the inner surface or sidewall 24 of the opening 22 of the orthopedic prosthesis 10 does not possess the groove 30 and the interference lip 704 may instead exert a compression force against the inner surface or sidewall 24 of the opening 22 to lock the osteoconductive device 700 in place. In some embodiments, the osteoconductive device 700 can include a plurality of interference lips placed as rings that encircle the sidewall 702 of the osteoconductive device 700. To be sure, the interference lip(s) disclosed with respect to the osteoconductive device 700 can be integrated into any of the osteoconductive devices disclosed herein.

Figure 9:
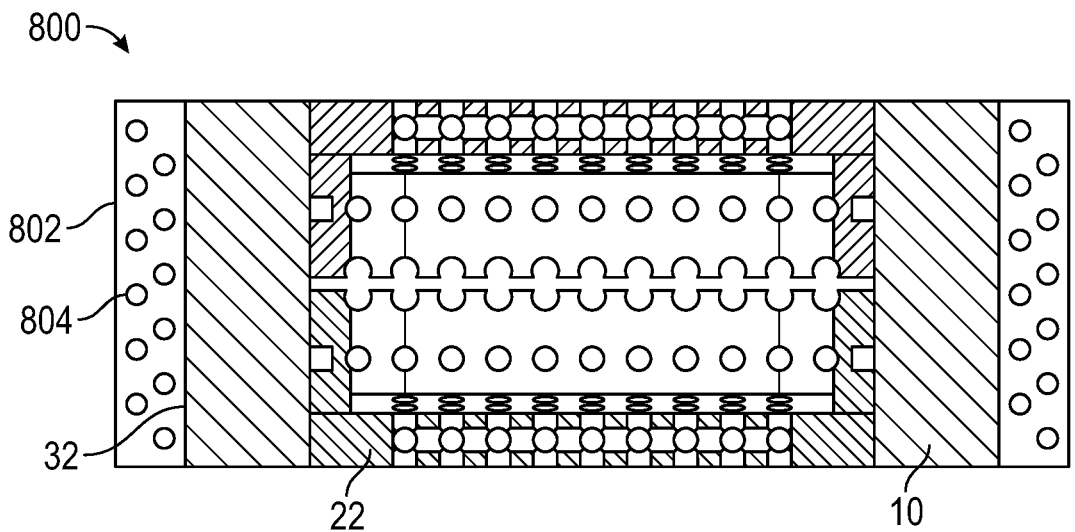
FIG. 9 illustrates another example embodiment of an osteoconductive device for use in combination with an orthopedic prosthesis.

FIG. 9 illustrates another osteoconductive device 800 that can be utilized in combination with an orthopedic prosthesis 10. Rather than being inserted into an opening 22 of an orthopedic prosthesis 10 the osteoconductive device 800 can be sized to fit around an outer peripheral surface 32 of the orthopedic prosthesis 10. In this embodiment, the osteoconductive device 800 has a body member that includes a sidewall 802 that can have porosity (e.g., apertures 804) and trenches as disclosed with other embodiments. The osteoconductive device 800 can be used in combination with any of the other osteoconductive devices disclosed herein. For example, the osteoconductive device 100 can be inserted into the opening 22 of an orthopedic prosthesis 10 while the osteoconductive device 800 is press fit around the outer peripheral surface 32 of the orthopedic prosthesis 10.

In other embodiments, an osteoconductive device as disclosed herein may not entirely fill the opening of the orthopedic prosthesis. Thus, the shape of the sidewall of an osteoconductive device need not completely conform to the inner surface or sidewall of the opening of the orthopedic prosthesis, but only portions of the sidewall may contact or engage with the inner surface or sidewall of the opening of the orthopedic prosthesis.

The osteconductive devices disclosed herein may be fabricated from traditional CNC (computer numerical control) and lathe operations but a method of making through additive manufacturing can also be utilized. Additive manufacturing allows for rapid production, rapid customization to any intervertebral cage, creation of macro surface roughness for increased titanium surface geometry, and simplified porous structural creations.

While some embodiments of osteconductive devices illustrate apertures that are circular the present disclosure should not be limited to the represented geometry. Thus, other geometrical shapes such as spherical, diamond, square, and so forth may be utilized.

Additionally, the osteconductive devices disclosed herein may be fabricated from titanium or a titanium blend but may alternatively be fabricated from any osteoconductive, osteoinductive, or other generally bone friendly material. Additional surface chemistry may be applied to any osteconductive device disclosed herein to enhance bone fusion.

Figure 10:
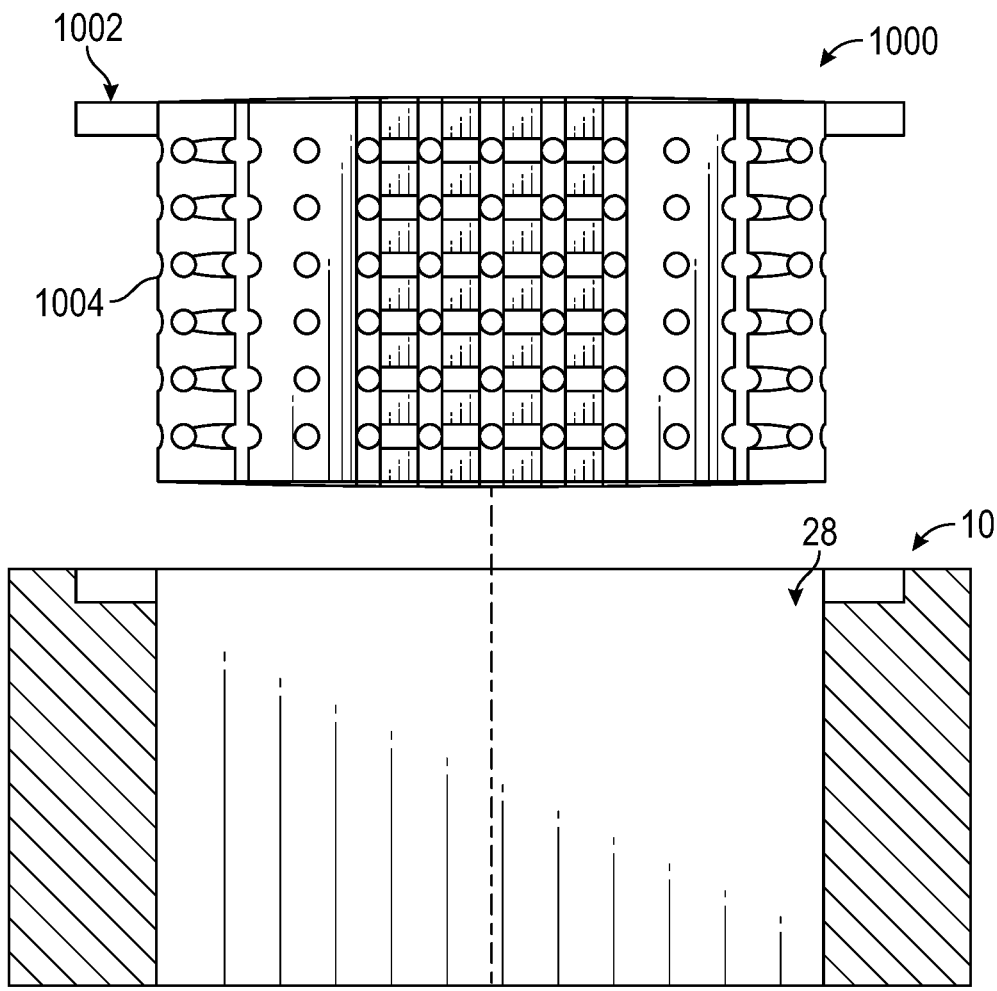
FIG. 10 is an exploded, cross-sectional view of yet another example embodiment of an osteoconductive device for use in combination with an orthopedic prosthesis

Referring to FIG. 10, one or more of the endplates of the orthopedic prosthesis 10 can be modified to receive a flange of an osteoconductive device 1000. That is, a flange 1002 of the osteoconductive device 1000 extends past a sidewall 1004 of the osteoconductive device 1000. The flange 1002 is received within a flange groove 28 fabricated into the endplate of the orthopedic prosthesis 10. The opposing endplate can be similarly modified to receive a flange of the second sidewall (not shown).

Example Embodiments

In some instances, the following examples may be implemented together or separately by the systems and methods described herein.

One embodiment includes an osteoconductive device, comprising a hollow body member comprising surfaces, the hollow body member having a shape that substantially conforms to a cross-sectional area of an opening of an orthopedic prosthesis; and apertures formed in the surfaces of the hollow body member that provide a osteoconductive path through the hollow body member.

In some instances, when the osteoconductive device is inserted into the opening of the orthopedic prosthesis, one of the surfaces of the hollow body member is substantially coplanar with a first surface of the orthopedic prosthesis and another surface of the hollow body member is substantially coplanar with a second surface of the orthopedic prosthesis, further wherein the first surface of the orthopedic prosthesis and the second surface of the orthopedic prosthesis are each outer surfaces of the orthopedic prosthesis.

In various instances the apertures are aligned to form rows. In some instances at least a portion of the first surface or the second surface is provided with any of surface roughening, additional porosity, or combinations thereof.

In one or more embodiments, the additional porosity comprises trenches formed across a portion of the rows to create a trench matrix defining surface objects.

According to some embodiments, a surface of the surfaces comprises protrusions that extend normally to surface, the protrusions being configured to engage with an inner sidewall of the opening of the orthopedic prosthesis, when the osteoconductive device is inserted into the bone fusion channel of the orthopedic prosthesis.

In various embodiments, a first surface of the surfaces is terminated to create a first shelf, and wherein a second surface of the surfaces is terminated to create a second shelf. In yet other embodiments, the surfaces comprise a first surface, a second surface, and a sidewall that spaces the first surface and the second surface away from one another, further wherein the sidewall engages with an inner surface of the opening of the orthopedic prosthesis.

In some instances, the surfaces comprise a first surface and a sidewall that extends normally from an outer peripheral edge of the first surface, further wherein the sidewall engages with an inner surface of the orthopedic prosthesis.

In various instances, the hollow body member comprises two portions, wherein a first of the two portions comprises a first surface of the surfaces; and a first sidewall that extends normally from an outer peripheral edge of the first surface. A second of the two portions comprise a second surface of the surfaces; and a second sidewall that extends normally from an outer peripheral edge of the second surface. The two portions are inserted into the opening of the orthopedic prosthesis in such a way that the first sidewall mates with or is in close proximity to the second sidewall.

In some instances, the first surface of the hollow body member is substantially coplanar with a first surface of the orthopedic prosthesis and the second of the hollow body member is substantially coplanar with a second surface of the orthopedic prosthesis.

In one or more embodiments, the present disclosure can be directed to a system comprising a spinal fusion cage comprising a bone fusion channel; and an osteoconductive device configured for insertion into the bone fusion channel of the spinal fusion cage, the osteoconductive device comprising a hollow body member comprising surfaces, the hollow body member having a shape that substantially conforms to an inner cross sectional area of the bone fusion channel, and apertures formed in the surfaces of the hollow body member that provide a osteoconductive path through the hollow body member.

In various embodiments, when the osteoconductive device is inserted into the bone fusion channel one of the surfaces of the hollow body member is substantially coplanar with a first surface of the spinal fusion cage and another surface of the hollow body member is substantially coplanar with a second surface of the spinal fusion cage.

In some embodiments, the apertures are aligned to form rows, further wherein at least a portion of the first surface or the second surface is provided with any of surface roughening, additional porosity, or combinations thereof.

In one or more embodiments, the additional porosity comprises trenches formed across a portion of the rows. In some instances, a surface of the surfaces comprises protrusions that extend normally to surface, the protrusions being configured to engage with an inner sidewall of the bone fusion channel when the osteoconductive device is inserted into the bone fusion channel of the orthopedic prosthesis.

In various embodiments, a first surface of the surfaces is terminated to create a first shelf and a second surface of the surfaces is terminated to create a second shelf.

In additional embodiments, the surfaces comprise a first surface, a second surface, and a sidewall that spaces the first surface and the second surface away from one another, further wherein the sidewall engages with an inner surface of the bone fusion channel, and further wherein the surfaces comprise a first surface and a sidewall that extends normally from an outer peripheral edge of the first surface, further wherein the sidewall engages with an inner surface of the bone fusion channel.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

While various embodiments of the present disclosure have been described above, it should be understood that they have been presented by way of example only, and not limitation. It will be apparent to persons skilled in the relevant art that various changes in form and detail can be made therein without departing from the spirit and scope of the present disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the present disclosure to the precise form disclosed. Many modifications and variations are possible in light of the above teaching. Further, it should be noted that any or all of the aforementioned alternate implementations may be used in any combination desired to form additional hybrid implementations of the present disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. An osteoconductive device comprising:
    a hollow body member comprising surfaces including a top wall, a bottom wall and a sidewall, each of the top wall, the bottom wall, and the sidewall cooperating to form an enclosed polygonal cavity, the enclosed polygonal cavity being defined by inner surfaces of each of the top wall, the bottom wall and the sidewall, the hollow body member having a shape that substantially conforms to a cross-sectional area of an opening of an orthopedic prosthesis; and
    apertures formed in each of the top and bottom walls of the hollow body member that provide an osteoconductive path through the hollow body member, the apertures being aligned to form rows, wherein a first set of sections of the sidewall comprises trenches formed across a portion of the rows to create a trench matrix defining surface objects, the trench matrix is capable of conducting bone into the sidewall and the surface objects contact an inner sidewall of the opening of the orthopedic prosthesis, wherein a second set of sections of the sidewall comprises sections having a flat surface area with no trenching, the first set of sections alternating with the second set of sections.

2. The osteoconductive device according to claim 1, wherein when the osteoconductive device is inserted into the opening of the orthopedic prosthesis, a top surface of the top wall of the hollow body member is substantially coplanar with a first surface of the orthopedic prosthesis and a bottom surface of the bottom wall of the hollow body member is substantially coplanar with a second surface of the orthopedic prosthesis, further wherein the first surface of the orthopedic prosthesis and the second surface of the orthopedic prosthesis are each outer surfaces of the orthopedic prosthesis.

3. The osteoconductive device according to claim 2, wherein at least a portion of the first surface or the second surface is provided with any of surface roughening, additional porosity, or combinations thereof.

4. The osteoconductive device according to claim 1, wherein a first surface of the surfaces is terminated to create a first shelf, and wherein a second surface of the surfaces is terminated to create a second shelf.

5. The osteoconductive device according to claim 1, wherein the sidewall spaces the top wall and the bottom wall away from one another.

6. The osteoconductive device according to claim 5, wherein the sidewall extends normally from the top wall.

7. A system comprising:
    a spinal fusion cage comprising a bone fusion channel; and
    an osteoconductive device configured for insertion into the bone fusion channel of the spinal fusion cage, the osteoconductive device comprising:
    a hollow body member comprising surfaces including a top surface of a top wall, a bottom surface of a bottom wall, and a sidewall, each of the top wall, the bottom wall, and the sidewall cooperating to form an enclosed cavity, the enclosed cavity being defined by inner surfaces of each of the top wall, the bottom wall, and the sidewall, the hollow body member having a shape that substantially conforms to an inner cross-sectional area of the bone fusion channel; and
    apertures formed in each of the top and bottom surfaces of the hollow body member that provide an osteoconductive path through the hollow body member, the apertures being aligned to form rows, wherein a first set of segments of the sidewall comprises trenches formed across a portion of the rows to create a trench matrix defining surface objects, wherein the trench matrix is capable of conducting bone into the sidewall and the surface objects contact an inner sidewall of the bone fusion channel of the spinal fusion cage, wherein a second set of sections of the sidewall comprises sections having a flat surface area with no trenching, the first set of sections alternating with the second set of sections.

8. The osteoconductive device according to claim 7, wherein when the osteoconductive device is inserted into the bone fusion channel, the top surface of the hollow body member is substantially coplanar with a first surface of the spinal fusion cage and the bottom surface of the hollow body member is substantially coplanar with a second surface of the spinal fusion cage.

9. The osteoconductive device according to claim 8, wherein at least a portion of the first surface or the second surface is provided with any of surface roughening, additional porosity, or combinations thereof.

10. The osteoconductive device according to claim 7, wherein a first surface of the surfaces is terminated to create a first shelf.

11. The osteoconductive device according to claim 10, wherein a second surface of the surfaces is terminated to create a second shelf.

12. The osteoconductive device according to claim 7, wherein the sidewall spaces the top wall and the second bottom wall away from one another, further wherein the sidewall engages with a peripheral surface of the spinal fusion cage that defines the bone fusion channel, and further wherein the sidewall extends normally from the top wall.

* * * * *